United States Patent [19]

Mees et al.

[11] Patent Number: 5,322,941
[45] Date of Patent: Jun. 21, 1994

[54] PROCESS FOR THE PREPARATION OF PYRENE COMPOUNDS

[75] Inventors: Bernhard Mees, Eppstein; Gerhard Zirkenbach, Rüdesheim, both of Fed. Rep. of Germany

[73] Assignee: Hoechst Aktiengesellschaft, Frankfurt, Fed. Rep. of Germany

[21] Appl. No.: 817,778

[22] Filed: Jan. 8, 1992

[30] Foreign Application Priority Data

Jan. 8, 1991 [DE] Fed. Rep. of Germany ....... 4100293

[51] Int. Cl.$^5$ .................. C07D 251/16; C07D 251/20
[52] U.S. Cl. ..................................... 544/217; 544/219
[58] Field of Search ................................ 544/217, 219

[56] References Cited

U.S. PATENT DOCUMENTS 3,156,690 11/1964 Dexter et al. ..................... 544/219
3,157,651 11/1964 Atkinson et al. .................. 544/219

FOREIGN PATENT DOCUMENTS 49-20195 6/1974 Japan ................................ 544/219

*Primary Examiner*—John M. Ford
*Attorney, Agent, or Firm*—Connolly and Hutz

[57] ABSTRACT

The invention relates to a process for the preparation of pyrene compounds of the formula

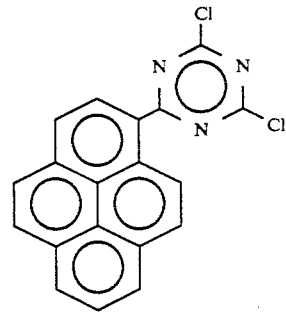

by reaction of cyanuric chloride with pyrene in the presence of an aluminum halide in an aromatic solvent in a Friedel-Crafts reaction, which comprises using as solvent non-polar, halogen-free aromatic compounds, preferably composed of methyl-, ethyl- and/or propyl-substituted benzene, and carrying out the reaction in the presence of non-aqueous bases, particularly carbonates of alkaline earth and alkali metals, bicarbonates of alkaline earth and alkali metals, and also alkali metal alcoholates of the formula MOR (R=$C_1$–$C_4$-alkyl, M=alkali metal).

16 Claims, No Drawings

PROCESS FOR THE PREPARATION OF PYRENE COMPOUNDS

The invention relates to a process for the preparation of a compound of the formula 1 and of the formula 2,

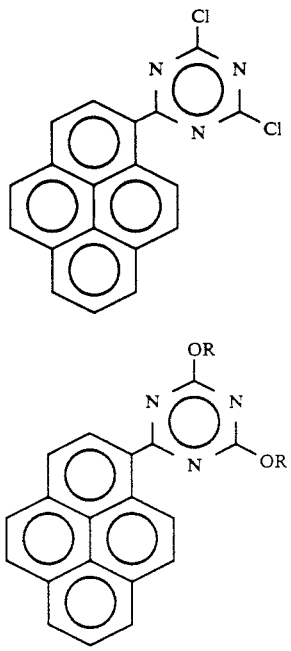

in which a complex of aluminum halide and cyanuric chloride is allowed to act on pyrene (Friedel-Crafts synthesis).

The compound of the formula 1 obtained can be reacted with alcoholates in a 2nd step to give products of the formula 2, which have attained industrial importance as optical brighteners for polyester and other plastics.

R can be alkyl, alkenyl, cycloalkyl, aralkyl or aryl. A process of this type has already been disclosed in EP-A-0 020 817 corresponds to U.S. Pat. No. 4,278,795 which is incorporated by reference.

It is known that high demands are placed on the purity of compounds used as optical brighteners. In the reaction of aluminum chloride with cyanuric chloride and pyrene to give the compound of the formula 1, compounds of the formulae 3 and 4 always result to a certain extent as unwanted byproducts:

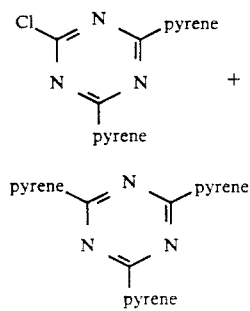

These compounds interfere during use of the compounds of the formula 2 as optical brighteners by strongly shifting the color towards green. In the process disclosed by EP-A-0 020 817, resort is made to the use as solvents of polar, in particular halogenated aromatic compounds, which do not participate in the reaction themselves, but possess good dissolving capacity for the impurities. However, these halogenated aromatic compounds are not ecologically desirable on a number of grounds. Use of non-halogenated aromatic compounds such as toluene or xylene as solvents does not, however, give acceptable product quality.

It is accordingly an object of the present invention to provide an efficient process leading to pure products of the formulae 1 and 2 in good yields, without needing to use ecologically unacceptable solvents.

According to the invention, this object is achieved by carrying out the Friedel-Crafts reaction using aluminum halide, cyanuric chloride and pyrene in the presence of small amounts of a non-aqueous base, halogen-free aromatic solvents being used. In this procedure, subsequent HPLC analysis of the resulting dichlorotriazinylpyrene compound does not show any contents of the unwanted di-and tripyrene compounds.

This effect of added non-aqueous bases is all the more surprising as these additions have not been previously known in Friedel-Crafts catalysis, and also contradict the concept of acid catalysis. The compound of the formula 1 is obtained in a yield of over 90%, relative to pyrene.

In carrying out the process it is expedient that the aluminum halide introduced into the anhydrous aromatic solvent receives an addition of 0.5-5% by weight of the non-aqueous base (% relative to the Al halide) with stirring at 0-35° C., preferably at 15-25° C.

The order of addition of the aluminum halide and the non-aqueous base to the aromatic solvent is not critical. It is, however, essential that the two compounds are stirred in the solvent in the cited temperature range for at least 5 minutes, preferably at least 10 minutes, prior to addition of the cyanuric chloride. Then at least an equivalent amount of cyanuric chloride in the halogen-free aromatic solvent is added, and the mixture is subsequently stirred in the same temperature range for at least a further 20 to 30 minutes. Subsequently, a solution of pyrene in the halogen-free aromatic solvent is slowly added dropwise with cooling, particularly at approximately 0-15° C., and then the mixture is stirred at room temperature for about 30 min to 3 hours. After completion of the reaction, the mixture is decomposed in water in a conventional manner, the product remaining in the aromatic upper phase.

After filtering off, washing and drying, the 2,4-dichloro-1,3,5-triazinylpyrene remains in the form of yellow crystals having a melting point of 258–259° C.

The product (formula 1) can be converted in a conventional manner in high yield to the corresponding compound of the formula 2, which, after filtration, washing and drying, can be used without further purification steps as an optical brightener. In the course of this, a compound of the formula MOR, in which R has the meaning given under formula 2 and M is alkali metal, is reacted at 50° to 80° C. with the product of the formula 1 in the anhydrous medium, particularly in ROH. The product of the formula 2 is also produced in high purity, so that no extensive purification steps are required.

The non-aqueous bases which can be used are, according to the invention, carbonates of alkaline earth and alkali metals, bicarbonates of alkaline earth and alkali metals and alkali metal alcoholares of $C_1$–$C_4$-alcohols. Examples which may be mentioned are sodium methylate, potassium methylate, sodium ethylate, potassium ethylate, sodium propylate, potassium propylate, sodium tert-butylate and potassium tert-butylate.

The aluminum halides which may be used are aluminum bromide and particularly aluminum chloride.

The halogen-free aromatic solvent is a methyl-, ethyl- and/or propyl-substituted benzene, preferably toluene and xylene, or a mixture of at least two of these compounds. The size and number of the alkyl groups are selected so that the solvent remains liquid under the reaction conditions. The total number of the carbon atoms of all the substituents should not exceed 6.

It is expedient to use 1–1.2 mol of both aluminum halide and cyanuric chloride per mole of pyrene. It is important that the non-aqueous base is stirred for a short time with the aluminum halide and that the solvent is anhydrous (water content below 0.1%).

The following examples are intended to illustrate the invention.

The pyrene is purified in greater detail by the following procedure:

104.9 g of pyrene (96.4% purity) are dissolved with stirring in 550 ml of redistilled, anhydrous, warm (50° C.) toluene, 5 g of bleaching earth (Tonsil®, produced by Süd-Chemie, Germany) are added for adsorptive decolorization and purification, and after 30 min, filtered off using a white ribbon filter.

The flask and filter are rinsed with 50 ml of anhydrous toluene.

EXAMPLE 1

300 ml of redistilled, anhydrous toluene are introduced into a 2 l four-necked flask equipped with stirrer, thermometer and calcium chloride tube, after flushing with nitrogen. Subsequently 81.6 g of $AlCl_3$ (98% pure) and 1.0 g of sodium methylate powder are introduced successively at room temperature with stirring, the mixture is stirred for 10 minutes at 25° C., and then 121.1 g of cyanuric chloride (99% pure) in xylene (anhydrous) are added. The mixture is stirred at the same temperature for about a further 30 min, then cooled to 5–10° C. Subsequently the purified pyrene solution is added dropwise over the course of 6 hours via a heated dropping funnel. After the addition is completed, the funnel is rinsed with 50 ml of toluene. The mixture is further stirred at room temperature, the reaction being complete after about 1 hour. The reaction mixture is forced during the course of 30 minutes into a mixture of 1.0 l of deionized water and 0.5 g of an emulsion breaker (previously dissolved in 20 ml of hot deionized water) with stirring, where a temperature of 45° C. is reached. The flask is rinsed with approximately 500 ml of deionized water and 50 ml of toluene. The resulting yellow suspension is refluxed for 1 hour (approximately 80° C.). The stirrer is stopped, and the lower phase is drained off after approximately 10 minutes.

In the same manner, the toluene phase is washed again at 80° C. for approximately 15 minutes with 750 ml of hot deionized water. After separation of the lower phase, 250 ml of deionized water are added and the mixture is maintained at 80° C. Then, the pH is adjusted to 4–5 using 6–8 g of a mixture of sodium bicarbonate and sodium acetate (1:1). Subsequently, the organic phase is filtered at approximately 40° C. using a heated pressure filter. The crystals, which are very easy to filter off, are washed with 150 ml of toluene in 3 portions, and 233.5 g of a filter cake, wetted by toluene and water, are obtained having a dry weight of 154.1 g and a melting point of 259° C. The yield is 91% of theory. A small sample, dissolved in tetrahydrofuran, shows no contents of the unwanted dipyrenyl compound (formula 3) and tripyrenyl compound (formula 4) in the HPLC using a Lichrosorb Si 60 column (5 μm) and a binary mobile phase mixture of n-hexane 90 (90%) and ethyl acetate (10%).

EXAMPLE 2

The process is carried out analogously to Example 1, the only difference being the use of potassium methylate powder instead of sodium methylate powder. The yield is 92% of theory. No dipyrenyl compound or tripyrenyl compound is detectable in the product.

The same result is achieved by the use of the following anhydrous bases: $KHCO_3$, $Na_2CO_3$, $K_2CO_3$, sodium ethylate, potassium ethylate, sodium propylate, potassium propylate, sodium butylate, and potassium butylate.

EXAMPLE 3

Previously purified pyrene (as described above) dissolved in toluene is added dropwise at 0–5° C. over the course of 8 hours to a mixture of 83 g of $AlCl_3$ (98% pure)

3 g of potassium tert-butylate and 125 g of cyanuric chloride (99%) in xylene (anhydrous).

After completion of the reaction the mixture is stirred for a further 2 hours at +20° C. and after decomposition in water is worked up according to Example 1.

The dichlorotriazinepyrene compound is obtained in a yield of 90% of theory. The melting point is 258.5° C. No dipyrenyl or tripyrenyl compounds are detectable in the product.

EXAMPLE 4

Previously purified pyrene (as described above) dissolved in toluene is added dropwise at 10–12° C. over the course of 10 hours to a mixture of 160 g of $AlBr_3$ (98% pure)

2 g of $NaHCO_3$ and 128 g of cyanuric chloride (99% pure) in xylene (anhydrous).

After completion of the reaction the mixture is stirred for a further 2 hours at approximately 25° C. and after decomposition in a mixture of ice/water in a ratio of 1:3 is worked up according to Example 1.

The dichlorotriazinylpyrene compound is obtained in a yield of 90% of theory. The melting point is 258.5° C. No dipyrenyl or tripyrenyl compounds are detectable in the product.

EXAMPLE 5 (COMPARISON EXAMPLE)

The Friedel-Crafts reaction is carried out according to Example 1, but without the addition of sodium methylate. A dipyrene content of 2.5% by weight is determined by HPLC analysis.

The product is not suitable as an optical brightener.

The products obtained in the examples are, as described in EP-A-0 020 817, reacted with the amount, at least equivalent to the exchangeable halogen atoms, of a compound of the formula MOR, in which M is an alkali metal, preferably sodium or potassium, and R is a $C_1$–$C_5$-alkyl, $C_2$–$C_5$-alkenyl, cyclohexyl, or phenyl which may be substituted by $C_1$–$C_3$-alkyl or by chlorine.

We claim:

1. A process for the preparation of pyrene compounds of the formula 1

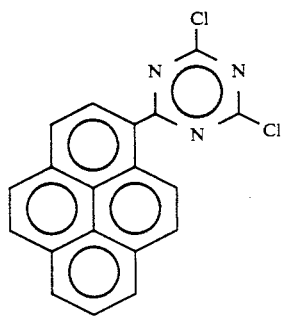

by reaction of cyanuric chloride with pyrene in the presence of an aluminum halide in an aromatic solvent in a Friedel-Crafts react, ion, which comprises using as solvent a non-polar, halogen-free aromatic compounds, and carrying out the reaction in the presence of a non-aqueous base.

2. The process as claimed in claim 1, wherein the non-aqueous base is added in a concentration of 0.5–5% by weight, relative to the aluminum halide.

3. The process as claimed in claim 1, wherein the aluminum halide used is aluminum chloride.

4. The process as claimed in claim 1, wherein the non-aqueous base used is sodium methylate.

5. The process as claimed in claim 1, wherein the solvent comprises toluene and/or xylene.

6. The process as claimed in claim 1, further comprising the pyrene compounds of the formula 1 are reacted with alcoholates to produce pyrene compounds of formula 2

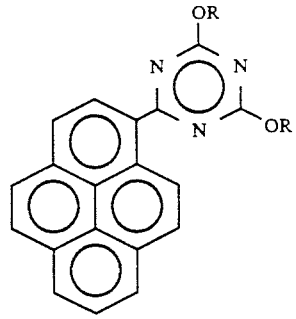

in which R represents an optionally substituted alkyl, alkenyl, cycloalkyl, aralkyl or aryl radical.

7. The process as claimed in claim 1, wherein the non-aqueous base is a carbonate of an alkaline earth or alkai metal, a bicarbonate of an alkaline earth or alkali metal, or an alkali metal alcoholate of the formula MOR, wherein R represents $C_1$–$C_4$-alkyl, and M represents an alkali metal.

8. The process as claimed in claim 1, wherein the non-polar, halogen-free aromatic compound comprises a methyl-, ethyl-, propyl-, methyl- and ethyl-, methyl- and propyl-, or ethyl- and propyl-substituted benzene.

9. The process as claimed in claim 2, wherein said aluminum halide is aluminum chloride.

10. The process as claimed in claim 6, wherein the pyrene compound obtained from claim 1 is converted to a pyrene compound of said formula 2 by reaction with a compound of the formula MOR, wherein R represents $C_1$–$C_4$-alkyl, and M represents an alkali metal.

11. The process as claimed in claim 1, wherein the resulting pyrene product of formula 1, notwithstanding the use of a non-polar, non-halogenated aromatic compound as solvent, is substantially free of byproducts which shift the color of the pyrene product toward green.

12. The process as claimed in claim 6, wherein the resulting pyrene product of formula 2 is substantially free of byproducts which shift the color of said pyrene product toward green.

13. The process as claimed in claim 6, wherein R is an alkyl, aralkyl, cycloalkyl or aryl.

14. The process as claimed in claim 6, wherein R is a substituted or unsubstituted $C_1$–$C_5$-alkyl, $C_2$–$C_5$-alkenyl, cyclohexyl, or phenyl.

15. The process as claimed in claim 6, wherein R is substituted by either a $C_1$–$C_3$-alkyl or chlorine.

16. The process as claimed in claim 14, wherein R is substituted by either a $C_1$–$C_3$-alkyl or chlorine.

* * * * *